(12) United States Patent
Jain et al.

(10) Patent No.: US 10,945,675 B2
(45) Date of Patent: Mar. 16, 2021

(54) DETERMINING A HEALTH STATUS FOR A USER

(71) Applicant: Samsung Electronics Co., Ltd., Gyeonggi-Do (KR)

(72) Inventors: Jawahar Jain, Los Altos, CA (US); James Young, Menlo Park, CA (US); Cody Wortham, Mountain View, CA (US); Sajid Sadi, San Jose, CA (US); Pranav Mistry, Campbell, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 359 days.

(21) Appl. No.: 15/957,570

(22) Filed: Apr. 19, 2018

(65) Prior Publication Data
US 2018/0338733 A1    Nov. 29, 2018

Related U.S. Application Data
(60) Provisional application No. 62/510,703, filed on May 24, 2017.

(51) Int. Cl.
*A61B 5/02* (2006.01)
*A61B 5/00* (2006.01)
(Continued)

(52) U.S. Cl.
CPC .......... *A61B 5/7275* (2013.01); *A61B 5/6802* (2013.01); *A61B 5/021* (2013.01);
(Continued)

(58) Field of Classification Search
CPC . A61B 5/7275; A61B 5/6802; A61B 5/02416; A61B 5/02405; A61B 5/14532;
(Continued)

(56) References Cited

U.S. PATENT DOCUMENTS

| | | | |
|---|---|---|---|
| 8,961,413 B2 | 2/2015 | Teller et al. | |
| 8,961,414 B2 | 2/2015 | Teller et al. | |

(Continued)

FOREIGN PATENT DOCUMENTS

| | | | |
|---|---|---|---|
| EP | 2542147 A2 | 1/2013 | |
| WO | WO2015033319 A2 | 12/2015 | |
| WO | WO2016110804 A1 | 12/2015 | |

OTHER PUBLICATIONS

Van Emmerik, R.E et al., "Comparing dynamical systems concepts and techniques for biomechanical analysis," Journal of Sport and Health Science, Mar. 1, 2016, vol. 5, No. 1, pp. 3-13.

(Continued)

*Primary Examiner* — Amanda K Hulbert
*Assistant Examiner* — Natasha Patel
(74) *Attorney, Agent, or Firm* — Cuenot, Forsythe & Kim, LLC

(57) ABSTRACT

Evaluating health of a user can include providing an equilibrium envelope for a user, wherein the equilibrium envelope includes a range for each of a plurality of vital signs, and detecting, using a processor, a current metric. The current metric corresponds to an exit condition for the equilibrium envelope determined based upon sensor data or a re-entry condition for the equilibrium envelope determined based upon the sensor data. A health status for the user can be determined, using the processor, based upon a comparison of the current metric with a historical metric for the user.

27 Claims, 3 Drawing Sheets

(51) Int. Cl.
A61B 5/0205 (2006.01)
A61B 5/021 (2006.01)
A61B 5/1455 (2006.01)
A61B 5/145 (2006.01)
A61B 5/024 (2006.01)

(52) U.S. Cl.
CPC ......... *A61B 5/0205* (2013.01); *A61B 5/02405* (2013.01); *A61B 5/02416* (2013.01); *A61B 5/14532* (2013.01); *A61B 5/14551* (2013.01)

(58) Field of Classification Search
CPC .... A61B 5/14551; A61B 5/021; A61B 5/0205
See application file for complete search history.

(56) References Cited

U.S. PATENT DOCUMENTS

| | | | |
|---|---|---|---|
| 9,028,405 | B2 | 5/2015 | Tran |
| 9,215,980 | B2 | 12/2015 | Tran et al. |
| 9,262,016 | B2 | 2/2016 | McGibney et al. |
| 9,313,418 | B2 | 4/2016 | Sethi |
| 9,421,422 | B2 | 8/2016 | Yuen et al. |
| 9,445,730 | B2 | 9/2016 | Snyder et al. |
| 9,448,164 | B2 | 9/2016 | Gulati et al. |
| 2007/0255122 | A1* | 11/2007 | Vol ................. A61B 5/6833 600/301 |
| 2008/0269583 | A1* | 10/2008 | Reisfeld ............ A61B 5/0402 600/364 |
| 2011/0245633 | A1* | 10/2011 | Goldberg ............ A61B 5/165 600/301 |
| 2014/0356966 | A1 | 12/2014 | Sethi |
| 2015/0250415 | A1 | 9/2015 | Leininger et al. |
| 2015/0324541 | A1 | 11/2015 | Cheung et al. |
| 2015/0374301 | A1 | 12/2015 | Teller et al. |
| 2017/0071523 | A1 | 3/2017 | Jain et al. |
| 2017/0071537 | A1 | 3/2017 | Jain et al. |
| 2017/0071551 | A1 | 3/2017 | Jain et al. |
| 2017/0156676 | A1* | 6/2017 | Ferber ............... A61B 5/02416 |
| 2017/0245808 | A1* | 8/2017 | Jain ................... A61B 5/746 |

OTHER PUBLICATIONS

Kurz, M.J. et al., "Attractor divergence as a metric for assessing walking balance," University of Nebraska, 2010, Journal Articles, Paper 135, 16 PG.
"HR & HRV Logger for Polar H7," [online] Google Apps, Google Inc. © 2018, Sep. 11, 2016 [retreived Apr. 18, 2018], retrieved from the Internet: <https://play.google.com/store/apps/details?id=hrmonitor.com.hr_rri_monitor&hl=en>, 2 pg.
"The Stress Eraser," [online] StressStop/AudioVision Inc. © 2009, [retrieved Apr. 18, 2018], retrieved from the Internet:. <http://www.stressstop.com/products/product.php?pid=79>, 2 pg.
"SweetWater Health and Stress," [online] SweetWater Health LLC © 2017, [retrieved Apr. 18, 2018], retrieved from the Internet: <http://www.sweetwaterhrv.com/Stress.shtml>, 3 pg.
"Stress Check by Azumio," [online] Azumio Inc., Google Apps, Google Inc. © 2018, Nov. 23, 2011, [retrieved Apr. 18, 2018], retrieved from the Internet <https://play.google.com/store/apps/details?id=com.azumio.android.stresscheck&hl=en_US>, 3 pg.
"BioHarness Data Logger and Telemetry System," [online] Biopac Systems, Inc. [retreived Apr. 18, 2018], retrieved from the Internet: <https://www.biopac.com/product/bioharness-telemetry-logging-systems/>, 5 pg.
"Stress Check," [online] AIIR Consulting LLC ™ 2009, [retreived Apr. 18, 2018], retrieved from the Internet <https://itunes.apple.com/us/app/stress-check/id330049595?mt=8>, 2 pg.
"Camera Heart Rate Variability," [online] A.S.M.A. B.V., © Marco Altini, [retrieved Apr. 18, 2018], retrieved from the Internet <https://itunes.apple.com/us/app/camera-heart-rate-variability/id788460316?mt=8>, 3 pg.
"Basis Peak Fitness and Sleep Tracker + Heart Rate Monitor," [online] Recreational Equipment, Inc. © 2018, [retreived Apr. 18, 2018], retrieved from the Internet: <https://www.rei.com/product/883367/basis-peak-fitness-and-sleep-tracker-heart-rate-monitor>, 12 pg.
Weisman, I.M. et al., "Clinical Exercise Testing," In Clinics in Chest Medicine, Dec. 1, 2001, vol. 22, No. 4, pp. 679-701, (abstract only).
Oken, B.S. et al., "A systems Approach to Stress, Stressors and Resilience in Humans," NIH Public Access Manuscript, 2014. 29 pg.
Resnick, B. et al., "Resilience in aging: Concepts, research, and outcomes," Springer Science & Business Media, 2010, 5 pg.
Doring, T.F. et al., "Resilience as a universal criterion of health," In Journal of the Science of Food and Agriculture, Feb. 2005, vol. 95, No. 3, pp. 455-465.
McCraty, R, et al. "Heart rate variability: new perspectives on physiological mechanisms, assessment of self-regulatory capacity, and health risk," In Global Advances in Health and Medicine, Jan. 2015, vol. 4, No. 1, pp. 46-61.
Winslow, B., et al., "Identification of resilient individuals and those at risk for performance deficits under stress," In Frontiers in neuroscience, Sep. 16, 2015, vol. 9, p. 328.
Norris, F.H., et al., "Looking for resilience: Understanding the longitudinal trajectories of responses to stress," In Social Science & Medicine, Jun. 1, 2009, vol. 68, No. 12, pp. 2190-2198.
Nemeth, C., et al., "Minding the gaps: creating resilience in health care," 2008, 13 pg.
Chetta, A, et al., "Reference values for the 6-min walk test in healthy subjects 20-50 years old," In Respiratory Medicine, Sep. 1, 2006, vol. 100, No. 9, pp. 1573-1578.
Alihanoglu, Y., et al., "Impaired systolic blood pressure recovery and heart rate recovery after graded exercise in patients with metabolic syndrome," In Medicine, Jan. 2015, vol. 94, No. 2, 6 pg.
Deniz, F. et al., "Association of metabolic syndrome with impaired heart rate recovery and low exercise capacity in young male adults," In Clinical Endocrinology, Feb. 2007, vol. 66, No. 2, pp. 218-223 (abstract only).
Dogan, U., et al., "Blunted heart rate recovery is associated with exaggerated blood pressure response during exercise testing," In Heart and Vessels, Nov. 1, 2013, vol. 28, No. 6, pp. 750-756.
Logan, JG, et al., "Allostasis and allostatic load: expanding the discourse on stress and cardiovascular disease," In Journal of Clinical Nursing, Jul. 1, 2008, vol. 17, No. 7b, pp. 201-208.
Karatsoreos, IN, et al., "Annual research review: The neurobiology and physiology of resilience and adaptation across the life course," In Journal of Child Psychology and Psychiatry, Apr. 2013, vol. 54, No. 4, pp. 337-347.
Solway, S, et al., "A qualitative systematic overview of the measurement properties of functional walk tests used in the cardiorespiratory domain," In Chest, Jan. 1, 2001, vol. 119, No. 1, pp. 256-270.

* cited by examiner

DETERMINING A HEALTH STATUS FOR A USER

CROSS-REFERENCE TO RELATED APPLICATIONS

This application claims the benefit of U.S. Provisional Patent Application No. 62/510,703 filed on May 24, 2017, which is fully incorporated herein by reference.

TECHNICAL FIELD

This disclosure relates to determining a health status for a user.

BACKGROUND

Many individuals wish to monitor their overall health. People engaged in a regular fitness program, for example, likely want to know whether their health is improving given their continued participation in the fitness program. Other people may have a known pathology and may want to know whether their health is improving with continued participation in a treatment program or other regimen for intervention.

Many individuals have turned to wearable devices for a solution. Often, these devices are capable of measuring a particular vital sign such as heart rate of the user. The devices show the measured vital sign to the user in real-time and/or store the vital sign measurements for subsequent review by the user. Observing heart rate alone and/or in isolation, however, does not provide sufficient information to determine whether the overall health of the user is improving.

To the extent that overall health of an individual can be measured, the testing needed is performed in a highly-controlled environment such as a hospital setting or in another medical facility. As such, the information needed to evaluate overall health of the user is costly and time-consuming to obtain. Further, the data that is collected is often limited to a snapshot that indicates the health status for the user at the particular moment in time when the data is collected.

SUMMARY

One or more embodiments are directed to methods of evaluating health of a user. In one aspect, a method can include providing an equilibrium envelope for a user, wherein the equilibrium envelope includes a range for each of a plurality of vital signs, and detecting, using a processor, a current metric. The current metric corresponds to an exit condition for the equilibrium envelope determined based upon sensor data or a re-entry condition for the equilibrium envelope determined based upon the sensor data. The method can include determining, using the processor, a health status for the user based upon a comparison of the current metric with a historical metric for the user.

One or more embodiments are directed to systems for evaluating health of a user. In one aspect, a system includes a memory configured to store instructions, a sensor configured to collect sensor data for a user, and a processor coupled to the memory. The processor, in response to executing the instructions, is configured to initiate operations for evaluating health of the user including providing an equilibrium envelope for a user, wherein the equilibrium envelope includes a range for each of a plurality of vital signs, and detecting a current metric. The current metric corresponds to an exit condition for the equilibrium envelope determined based upon the sensor data or a re-entry condition for the equilibrium envelope determined based upon the sensor data. The operations can include determining a health status for the user based upon a comparison of the current metric with a historical metric for the user.

One or more embodiments are directed to computer program products for evaluating health of a user. In one aspect, a computer program product includes a computer readable storage medium having program code stored thereon. The program code is executable by a processor to perform executable operations. The executable operations can include providing an equilibrium envelope for a user, wherein the equilibrium envelope includes a range for each of a plurality of vital signs, and detecting a current metric. The current metric corresponds to an exit condition for the equilibrium envelope determined based upon sensor data or a re-entry condition for the equilibrium envelope determined based upon the sensor data. The executable operations can include determining a health status for the user based upon a comparison of the current metric with a historical metric for the user.

This Summary section is provided merely to introduce certain concepts and not to identify any key or essential features of the claimed subject matter. Many other features and embodiments of the invention will be apparent from the accompanying drawings and from the following detailed description.

BRIEF DESCRIPTION OF THE DRAWINGS

The accompanying drawings show one or more embodiments; however, the accompanying drawings should not be taken to limit the invention to only the embodiments shown. Various aspects and advantages will become apparent upon review of the following detailed description and upon reference to the drawings.

DETAILED DESCRIPTION

Figure 1:
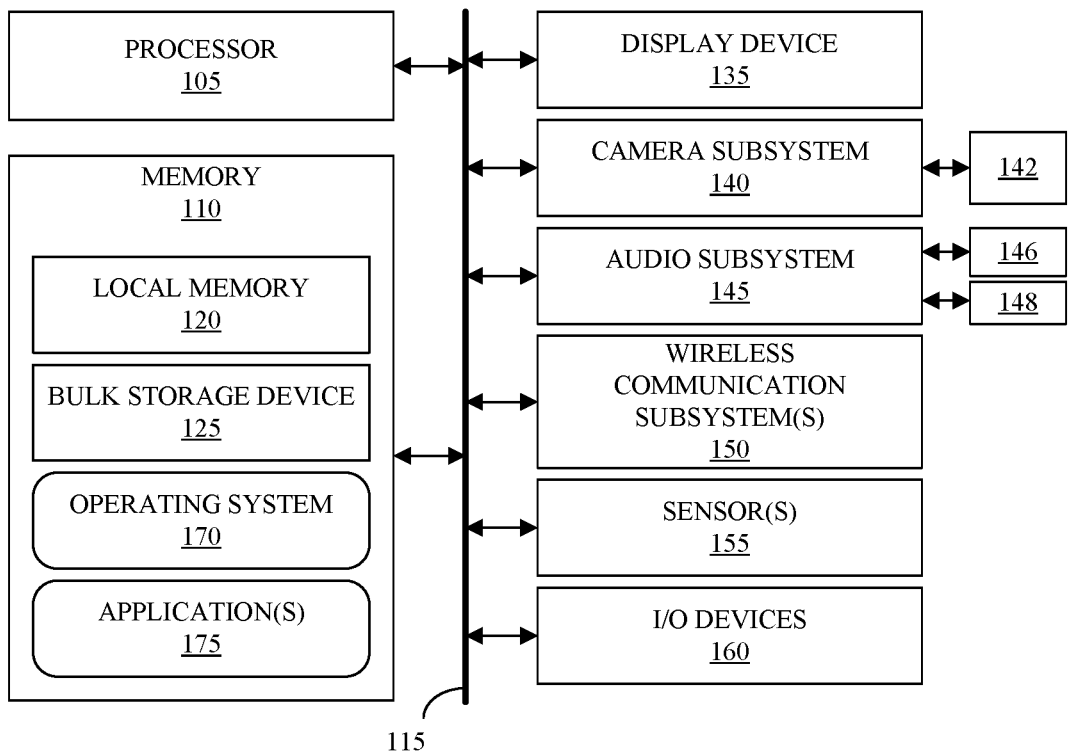
FIG. 1 illustrates an example device for use with one or more embodiments described within this disclosure.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to determining health status of a user. In accordance with the inventive arrangements described within this disclosure, user activities may be tracked over time with the aid of a device having one or more sensors. For example, a device outfitted with one or more sensors is capable of measuring vital signs of the user. The device is capable of comparing the vital sign measurements with an equilibrium envelope of the user. The device is further capable of determining one or more metrics relating to the measured vital signs and the equilibrium envelope. Through a comparison of the metric(s) with historical metric(s) for the user, the device is capable of determining a health status for the user. For example, the device is capable of determining and/or indicating whether the overall health of the user is increasing, decreasing, or has remained largely unchanged over time.

As defined within this disclosure, the term "equilibrium envelope" means two or more ranges, where each range corresponds to one vital sign. Each range defines the set of possible values for a given vital sign that is indicative of homeostatic equilibrium for the user while the user is at rest. In general, homeostatic equilibrium refers to the tendency of a biological system, e.g., a user, to maintain relatively constant conditions in the internal environment while continuously interacting with, and adjusting to, changes originating within or outside the biological system. Each range of the equilibrium envelope for the user specifies a baseline state of homeostatic equilibrium for a vital sign with the user at rest.

In particular embodiments, the metrics correspond to states where the user exits and/or re-enters the equilibrium envelope. The metric(s) can be compared with historical metrics for the user relating to the user exiting and/or re-entering the equilibrium envelope. In one or more embodiments, the metrics measure time. For example, the metrics may measure time for an exit condition to occur and/or time for a re-entry condition to occur. In one or more embodiments, the metrics measure a quantity or amount of an activity that is performed by the user. For example, the metrics may measure the quantity of an activity that is performed by the user for an exit condition to occur. Accordingly, the device is capable of determining whether a given metric has improved in relation to a historical metric for the user indicating an improvement in health status for the user, declined in relation to the historical metric for the user indicating a decline in the health status for the user, or remained the same or largely unchanged in relation to the historical metric for the user indicating little or no change to the health status for the user.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example of a device 100 for use with one or more embodiments described within this disclosure. Device 100 includes at least one processor 105. Processor 105 is coupled to memory 110 through interface circuitry 115. Device 100 stores computer readable instructions (also referred to as "program code") within memory 110. Memory 110 is an example of computer readable storage media. Processor 105 executes the program code accessed from memory 110 via interface circuitry 115.

Memory 110 includes one or more physical memory devices such as, for example, a local memory 120 and a bulk storage device 125. Local memory 120 is implemented as one or more non-persistent memory devices used during actual execution of the program code. Examples of local memory 120 include random-access memory (RAM) and/or any of the various types of RAM (e.g., static RAM, dynamic RAM) that are suitable for use by a processor during execution of program code. Bulk storage device 125 is implemented as one or more persistent data storage devices. Examples of bulk storage device 125 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Device 100 may also include one or more cache memories (not shown) that provide temporary storage of at least some program code in order to reduce the number of times program code must be retrieved from a bulk storage device during execution.

Examples of interface circuitry 115 include, but are not limited to, an input/output (I/O) subsystem, an I/O interface, a bus system, and a memory interface. For example, interface circuitry 115 may be implemented as any of a variety of bus structures and/or combinations of bus structures including a memory bus or memory controller, a peripheral bus, an accelerated graphics port, and a processor or local bus.

In one or more embodiments, processor 105, memory 110, and/or interface circuitry 115 are implemented as separate components. In one or more embodiments, processor 105, memory 110, and/or interface circuitry 115 are integrated in one or more integrated circuits. The various components in device 100, for example, can be coupled by one or more communication buses or signal lines (e.g., interconnects and/or wires). In particular embodiments, memory 110 is coupled to interface circuitry 115 via a memory interface, e.g., a memory controller (not shown).

Device 100 may include a display 135. In particular embodiments, display 135 is implemented as touch-sensitive or touchscreen display capable of receiving touch input from a user. A touch sensitive display and/or a touch-sensitive pad is capable of detecting contact, movement, gestures, and breaks in contact using any of a variety of available touch sensitivity technologies. Example touch sensitive technologies include, but are not limited to, capacitive, resistive, infrared, and surface acoustic wave technologies, and other proximity sensor arrays or other elements for determining one or more points of contact with a touch sensitive display and/or device.

Device 100 may include a camera subsystem 140. Camera subsystem 140 can be coupled to interface circuitry 115 directly or through a suitable input/output (I/O) controller. Camera subsystem 140 can be coupled to an optical sensor 142. Optical sensor 142 may be implemented using any of a variety of technologies. Examples of optical sensor 142 can include, but are not limited to, a charged coupled device (CCD) or a complementary metal-oxide semiconductor (CMOS) optical sensor. Camera subsystem 140 and optical sensor 142 are capable of performing camera functions such as recording images and/or recording video.

Device 100 may include an audio subsystem 145. Audio subsystem 145 can be coupled to interface circuitry 115 directly or through a suitable input/output (I/O) controller. Audio subsystem 145 can be coupled to a speaker 146 and a microphone 148 to facilitate voice-enabled functions, such as voice recognition, voice replication, digital recording, and telephony functions.

Device 100 may include one or more wireless communication subsystems 150. Each of wireless communication subsystem(s) 150 can be coupled to interface circuitry 115 directly or through a suitable I/O controller (not shown). Each of wireless communication subsystem(s) 150 is capable of facilitating communication functions. Examples of wireless communication subsystems 150 can include, but are not limited to, radio frequency receivers and transmitters, and optical (e.g., infrared) receivers and transmitters. The specific design and implementation of wireless communication subsystem 150 can depend on the particular type of device 100 implemented and/or the communication network(s) over which device 100 is intended to operate.

As illustrative and non-limiting examples, wireless communication subsystem(s) 150 may be designed to operate over one or more mobile networks (e.g., GSM, GPRS, EDGE), a WiFi network which may include a WiMax network, a short range wireless network (e.g., a Bluetooth network), and/or any combination of the foregoing. Wireless communication subsystem(s) 150 can implement hosting protocols such that device 100 can be configured as a base station for other wireless devices.

Device 100 may include one or more sensors 155. Each of sensors 155 can be coupled to interface circuitry 115 directly or through a suitable I/O controller (not shown). Examples of sensors 155 that can be included in device 100 include, but are not limited to, a motion sensor, a light sensor, and a proximity sensor to facilitate orientation, lighting, and proximity functions, respectively, of device 100. Other examples of sensors 155 can include, but are not limited to, a location sensor (e.g., a GPS receiver and/or processor) capable of providing geo-positioning sensor data, an electronic magnetometer (e.g., an integrated circuit chip) capable of providing sensor data that can be used to determine the direction of magnetic North for purposes of directional navigation, an accelerometer capable of providing data indicating change of speed and direction of movement of device 100 in 3-dimensions, and an altimeter (e.g., an integrated circuit) capable of providing data indicating altitude.

In one or more embodiments, sensors 155 include a photoplethysmogram (PPG) sensor. A PPG sensor is a type of optical sensor. A PPG sensor is capable of generating a PPG for the user. A PPG is an optically obtained plethysmogram. In general, a PPG is a volumetric measurement of an organ. In one or more embodiments, a PPG sensor is implemented as a pulse oximeter which illuminates the skin and measures changes in light absorption to determine amount of oxygen carried in the blood. The PPG sensor can be used to determine one or more vital signs and/or to determine one or more surrogate markers of one or more vital signs.

Device 100 further may include one or more input/output (I/O) devices 160 coupled to interface circuitry 115. I/O devices 160 may be coupled to device 100, e.g., interface circuitry 115, either directly or through intervening I/O controllers (not shown). Examples of I/O devices 160 include, but are not limited to, a track pad, a keyboard, a display device, a pointing device, one or more communication ports (e.g., Universal Serial Bus (USB) ports), a network adapter, and buttons or other physical controls. A network adapter refers to circuitry that enables device 100 to become coupled to other systems, computer systems, remote printers, and/or remote storage devices through intervening private or public networks. Modems, cable modems, Ethernet interfaces, and wireless transceivers not part of wireless communication subsystem(s) 150 are examples of different types of network adapters that may be used with device 100. One or more of I/O devices 160 may be adapted to control functions of one or more or all of sensors 155 and/or one or more of wireless communication subsystem(s) 150.

Memory 110 stores program code. Examples of program code include, but are not limited to, routines, programs, objects, components, logic, and other data structures. For purposes of illustration, memory 110 stores an operating system 170 and application(s) 175. Operating system 170 and/or applications 175 can include, for example, health status program code (e.g., a health status application). In one or more embodiments, the health status program code, when executed, is capable of causing device 100 and/or other devices that may be communicatively linked with device 100, to perform the various operations described herein. Memory 110 is also capable of storing data, whether data utilized by operating system 170, data utilized by application(s) 175, data received from user inputs, data generated by one or more or all of sensor(s) 155, data received and/or generated by camera subsystem 140, data received and/or generated by audio subsystem 145, and/or data received by I/O devices 160.

In an aspect, operating system 170 and application(s) 175, being implemented in the form of executable program code, are executed by device 100 and, more particularly, by processor 105, to perform the operations described within this disclosure. As such, operating system 170 and application(s) 175 may be considered an integrated part of device 100. Further, it should be appreciated that any data and/or program code used, generated, and/or operated upon by device 100 (e.g., processor 105) are functional data structures that impart functionality when employed as part of device 100.

Memory 110 is capable of storing other program code. Examples of other program code include, but are not limited to, instructions that facilitate communicating with one or more additional devices, one or more computers and/or one or more servers; graphic user interface (GUI) and/or UI processing; sensor-related processing and functions; phone-related processes and functions; electronic-messaging related processes and functions; Web browsing-related processes and functions; media processing-related processes and functions; GPS and navigation-related processes and functions; security functions; and camera-related processes and functions including Web camera and/or Web video functions.

Device 100 further can include a power source (not shown). The power source is capable of providing electrical power to the various elements of device 100. In an embodiment, the power source is implemented as one or more batteries. The batteries may be implemented using any of a variety of known battery technologies whether disposable (e.g., replaceable) or rechargeable. In another embodiment, the power source is configured to obtain electrical power from an external source and provide electrical power (e.g., direct current (DC) power) to the elements of device. In the case of a rechargeable battery, the power source further may include circuitry that is capable of charging the battery or batteries when coupled to an external power source.

Device 100 is provided for purposes of illustration and not limitation. A device and/or system configured to perform the operations described herein may have a different architecture than illustrated in FIG. 1. The architecture may be a simplified version of the architecture described in connection with FIG. 1 that includes a memory capable of storing instructions and a processor capable of executing instructions. In this regard, device 100 may include fewer components than shown or additional components not illustrated in FIG. 1 depending upon the particular type of device that is implemented. In addition, the particular operating system and/or application(s) included may vary according to device type as may the types of I/O devices 160 included. Further, one or more of the illustrative components may be incorporated into, or otherwise form a portion of, another component. For example, a processor may include at least some memory.

Device 100 may be implemented as a data processing system, a communication device, or other suitable system that is suitable for storing and/or executing program code. Example implementations of device 100 may include, but are not to limited to, a smart phone or other mobile device or phone, a wearable computing device (e.g., a smart watch), a computer (e.g., desktop, laptop, or tablet computer), and/or a television or other appliance with a display (e.g., an exercise machine).

Figure 2:
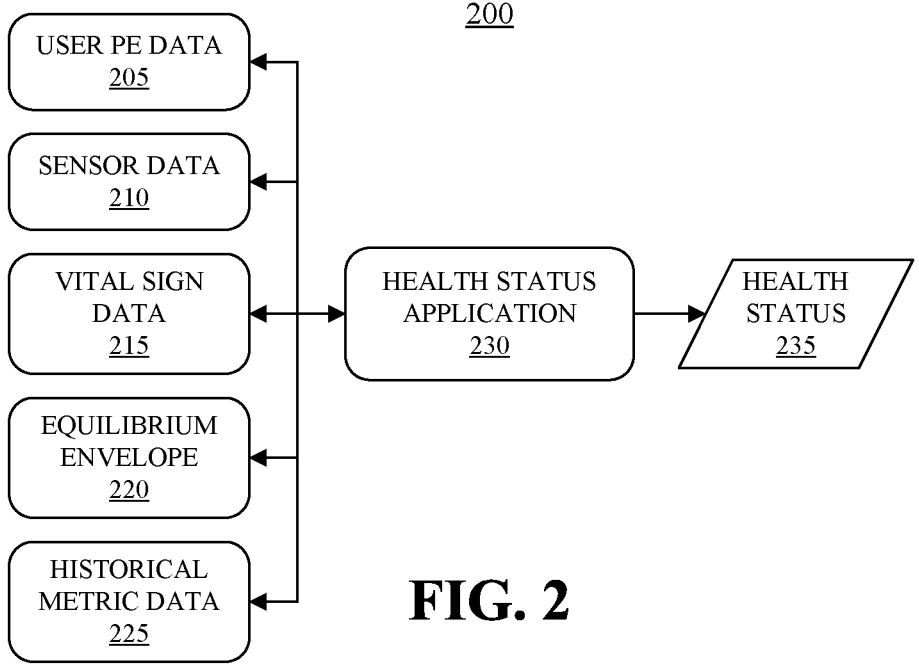
FIG. 2 illustrates an example software architecture for use with one or more embodiments described within this disclosure.

FIG. 2 illustrates an example software architecture 200 for use with one or more embodiments described within this disclosure. Software architecture 200 is executable by a data processing system such as device 100 as described herein in connection with FIG. 1. In the example of FIG. 2, software architecture 200 includes user perceived exertion (PE) data 205, sensor data 210, an equilibrium envelope 215, and historical metric data 225. Each of user PE data 205, sensor data 210, equilibrium envelope 215, and historical metric data 225 is user-specific data.

User PE data 205 is data stored in a memory of device 100 that specifies a user PE level for each of one or more different activities. The range of activities stored in user PE data 205 may vary from different types of exercises to different everyday activities of the sort used to evaluate a person's level of independence. Examples of different exercises include walking, running, biking, and/or swimming. A quantity for the activity may be associated with each exercise. The quantity may be specified in a variety of different ways. For example, the quantity can be specified as an amount of time for performing the exercise, as a distance, as a number of steps, and/or as an amount of power (e.g., wattage from an accelerometer). Examples of everyday activities include opening a door, pouring a glass of water, making the bed, bathing, and/or changing clothes. In the case of certain activities such as, for example, opening a door, pouring a glass of water, making the bed, bathing, and/or changing clothes, a quantity of the activity may not be included in user PE data 205. For each activity, a user PE level from the user may be stored. As such, in one or more embodiments, user PE data 205 may include a plurality of entries stored over time (e.g., historical data) where each entry may specify a quantity and/or a user specified PE level.

As an illustrative and non-limiting example, the user may enter user PE levels while performing a particular activity. In one or more embodiments, the device is capable of determining the activity that the user is performing automatically. For example, the device is capable of determining the activity that the user is performing based upon detected accelerometer data. Further, the device is capable of automatically determining when the activity starts using the same or similar sensor data (e.g., accelerometer and GPS sensor data). In particular embodiments, the user provides one or more user inputs to the device indicating the particular activity that the user is engaging in and/or indicating when (e.g., a time) when the user starts performing the activity.

Subsequently, while performing the activity and/or after performing the activity, the user provides a user input to device 100 specifying a user PE level for the activity. The user PE level can be specified as a numerical value on a scale such as 1-3, 1-5, or 1-10. In another example the user PE level can be specified as "easy", "medium", or "hard". The user PE level can be stored in association with the activity and optionally a quantity of the activity performed, whether as a number of steps, distance, time, or other suitable measure of quantity. As noted, in the case of some activities such as bathing, making the bed, or other everyday activities, a quantity need not be specified.

Sensor data 210 is data generated and/or obtained from sensor(s) 155 that is stored in a memory of device 100. In one or more embodiments, sensor data 210 includes PPG data, e.g., one or more PPGs taken continuously and/or over time by device 100. PPG data provides surrogate markers for one or more different vital signs. As device 100 executes, device 100 is capable of continuing to store sensor data 210 over time, thereby storing sensor data 210 in real-time and generating a history of such sensor data. While PPG data is discussed, sensor data 210 may include sensor data collected from any of the various sensors 155 described herein under various conditions such as during an activity or exertion and post exertion (e.g., after having stopped an activity).

In one or more embodiments, device 100, in executing health status application 230, is capable of determining one or more vital signs for the user from sensor data 210, e.g., the PPG data. Device 100 is capable of determining, e.g., calculating, one or more vital signs from sensor data 210 and storing the vital signs, e.g., measures of vital signs, as vital sign data 215. Device 100 is capable of determining vital signs including, but not limited to, heart rate (e.g., heart beats per minute), blood pressure, and respiration (e.g., respiratory rate typically measured in breaths per minute) from PPG data. Device 100 is capable of determining vital signs including, but not limited to, heart rate variability, oxygen saturation, and blood glucose from PPG data. Device 100 is capable of storing a measure for each of the different vital signs discussed within vital sign data 215.

As an illustrative and non-limiting example, PPG data collected using a pulse oximetry sensor to measure O2 saturation can be used to determine respiratory rate since the PPG reflects blood volume changes, which are caused by respiration. For example, respiratory sinus arrhythmia (RSA) can be used in combination with PPG volume trend and frequency component change from a PPG to determine respiratory rate for the user.

As another example, the area under the curve (AUC) of the PPG may be used as a surrogate marker for blood pressure. Device 100, for example, is capable of determining systolic blood pressure for the user based upon the AUC of a PPG waveform. Larger AUC corresponds to higher systolic blood pressure. As an illustrative and non-limiting example, some studies have found that very low frequency (VLF) fluctuations of systolic blood pressure are related to PPG where systolic blood pressure was found to have a correlation coefficient of approximately −0.81 with VLF fluctuations of PPG amplitude (AM) and a correlation coefficient of approximately 0.83 with PPG baseline (BL) over 10-minute time periods.

In another example, device 100 can determine stroke volume from PPG data. In illustration, blood pressure, which can be determined using AUC of the PPG, generally equals cardiac output times total peripheral resistance. Device 100 can determine cardiac output since cardiac output from PPG data since cardiac output is calculated as the amount of blood pumped out of the heart per beat (stroke volume) multiplied by heart rate (number of beats per minute). PPG RR interval (where "RR" is the interval between successive Rs and R represents a peak of the PPG) can be used to determine heart rate and heart rate variability. Heart rate variability or "HRV" is the physiological phenomenon of variation in the time interval between heart beats. Heart rate variability is measured by the variation in the beat-to-beat interval.

In one or more embodiments, sensor data 210 includes sensor data collected for the user while at homeostatic equilibrium. Such sensor data can be used to generate a range for one or more or each of the vital signs measured. For example, device 100 is capable of determining a range having an upper bound and a lower bound for one or more or any combination of vital signs such as of heart rate, blood pressure, respiration, heart rate variability, oxygen saturation, and blood glucose.

Equilibrium envelope 215 specifies two or more ranges for vital signs for the user. In one or more embodiments, equilibrium envelope 215 specifies a range for heart rate and range for blood pressure for the user. In one or more embodiments, equilibrium envelope 215 specifies a range for heart rate, a range for blood pressure, and a range for respiration. In one or more embodiments, equilibrium envelope specifies a range for heart rate, a range for blood pressure, a range for respiration, and a range for heart rate variability. In one or more embodiments, equilibrium envelope specifies a range for heart rate, a range for blood pressure, a range for respiration, a range for heart rate variability, and a range for oxygen saturation. In one or more embodiments, equilibrium envelope specifies a range for heart rate, a range for blood pressure, a range for respiration, a range for heart rate variability, a range for oxygen saturation, and a range for blood glucose.

Equilibrium envelope 220 can include any combination of two or more ranges, where each range is for a different vital sign measured for the user while the user is in homeostatic equilibrium and at rest. In one or more embodiments, equilibrium envelope 220 may be programmed or otherwise loaded into memory of device 100. In particular embodiments, health status application 230 is capable of accessing sensor data 210 and/or vital sign data 215 to generate equilibrium envelope 220 to include or specify two or more ranges. For example, health status application 230 is capable of determining, based upon accelerometer data and/or user inputs, whether the user is at rest to collect sensor 210 and/or determine vital sign data 215 to generate equilibrium envelope 220.

Health status application 230 is capable of generating and storing historical metric data 225. Historical metric data 225 includes one or more metrics determined for the user over time. In one or more embodiments, the metric(s) correspond to an exit condition for equilibrium envelope 220. An exit condition refers to the situation where the user performs an activity and, in response to performing the activity, one or more of the vital signs for the user move out of the established range for that vital sign as specified by equilibrium envelope 220.

In one or more embodiments, the metric(s) correspond to a re-entry condition for equilibrium envelope 220. A re-entry condition refers to the situation where an exit condition has occurred and, while one or more or all of the vital signs of equilibrium envelope 220 are outside of the respective established ranges, the user discontinues the activity. The re-entry condition occurs when each vital sign for which equilibrium envelope 220 specifies a range has moved back into the respective, established range as specified by equilibrium envelope 220.

In particular embodiments, the metrics specify time. A metric, for example, may specify the amount of time measured from the start of an activity until an exit condition for the user is detected. In particular embodiments, the metric specifies the amount of time from discontinuing an activity before a re-entry condition is detected (presuming that an exit condition was previously detected). In particular embodiments, the metric specifies a quantity of activity. For example, the metrics may specify a quantity or amount of an activity that the user performs in order to cause an exit condition. Further details about the metrics are described with reference to the remaining figures.

Health status application 230 is capable of determining a metric or metrics in real-time or in substantially real-time. Health status application 230 is capable of comparing a metric determined in real-time (e.g., a "current metric") relating to an exit condition and/or a re-entry condition with a prior determined metric (e.g., a historical metric) from historical metric data 225. Health status application 230 is capable of outputting a health status 235 for the user based upon the comparison of the current metric with the historical metric.

As the user performs daily activities, the vital signs of the user may vary, but should stay within the respective ranges of equilibrium envelope 220. Conditions relating to exit from the equilibrium envelope and/or re-entry to the equilibrium envelope can be evaluated and compared with historical conditions for the user. The metrics provide a means of quantifying these conditions and, as such, provide an indication of the health status for the user when compared with historical metrics.

Figure 3:
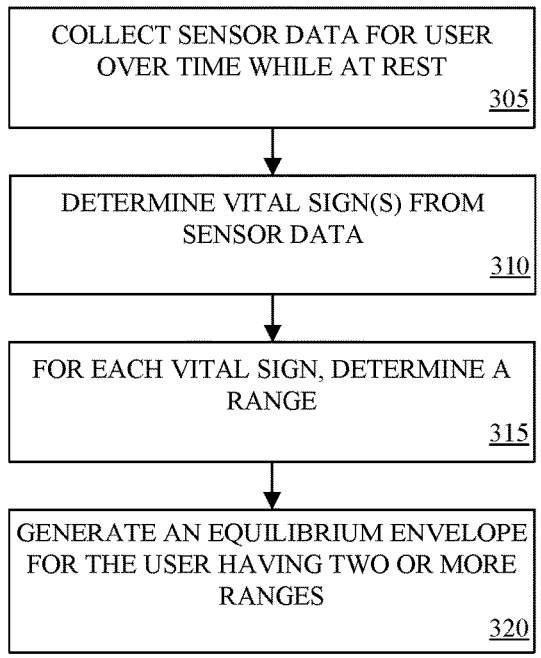
FIG. 3 illustrates an example method for determining an equilibrium envelope.

FIG. 3 illustrates an example method 300 for determining an equilibrium envelope for a user. Method 300 can be performed by device 100 as described in connection with FIG. 1.

In block 305, the device collects sensor data for the user over time. The sensor data is collected while the user is at rest in homeostatic equilibrium. For example, the device is capable of collecting PPG data for the user over time while the user is at rest in homeostatic equilibrium. a respiratory sensor.

In one or more embodiments, the device is capable of automatically detecting that the user is at rest and, in response, begin collecting sensor data for determining vital signs. For example, the device is capable of collecting sensor data from motion sensors (e.g., accelerometer data and/or GPS data). In response to determining that the user is at rest, e.g., moving less than a predetermined amount, is stationary, and/or is expending less than a threshold amount of energy, the device is capable of automatically collecting sensor data such as PPG data.

In particular embodiments, the device is capable of receiving an input from the user indicating that the user is at rest and/or in homeostatic equilibrium. In response to the input, the device is capable of automatically collecting sensor data such as PPG data. The device is capable of collecting sensor data for a predetermined period of time and/or until the device determines that the user is no longer at rest. The device is capable of determining that the user is no longer at rest based upon another received user input indicating such a state and/or based upon motion sensor data indicating that more than a threshold amount of energy is detected and/or more than a threshold amount of motion is detected.

In block 310, the device determines one or more vital signs from the sensor data. For example, the device is capable of generating a measurement for heart rate, a measurement for blood pressure, a measurement for respiration, a measurement for heart rate variability, a measurement for oxygen saturation, and a measurement for blood glucose from the PPG data. The device is capable of generating values for the noted vital signs over time while the user is at rest.

In block 315, the device determines a range for each vital sign determined in block 310. In one or more embodiments, the device is capable of determining a high measurement and a low measurement for each range for each vital sign for the time period while the device collects sensor data with the user being at rest.

In block 320, the device generates an equilibrium envelope for the user. The equilibrium envelope includes two or more of the ranges generated in block 315. As noted, the equilibrium envelope can include a range for any combination of two or more of the vital signs described.

In one or more embodiments, the device is capable of determining a range for each vital sign by taking the lowest and the highest measurement for the vital sign over the time period where the vital sign is measured with the user at rest. In one or more embodiments, the device is capable of determining a range for each vital sign by taking an average of the lowest "N" measurements for the vital sign for the low end of the range and by taking an average of the highest "N" measurements for the vital sign for the high end of the range. It should be appreciated that the device may apply any of a variety of statistical processing methods to determine the upper and lower bound of each range and, as such, the inventive arrangements described herein are not intended to be limited by the particular examples provided.

Method 300 describes an example method for automatically generating an equilibrium envelope. Method 300 is provided as an example and is not intended to be limiting of the inventive arrangements described herein. In one or more embodiments, the device is capable of receiving the equilibrium envelope by way of one or more user inputs specifying such data. For example, the user, a medical service provider, or other person may manually enter the equilibrium envelope into the device using a user interface generated by the health status application. In one or more other embodiments, the equilibrium envelope for the user may be determined using another system and provided to the device (e.g., imported into the device) from the other computing system. For example, a computing system of a medical service provider may determine the equilibrium envelope for the user based upon sensor data available or stored in the other computing system and/or provided to the other computing system and provide the equilibrium envelope to the user's device.

Figure 4:
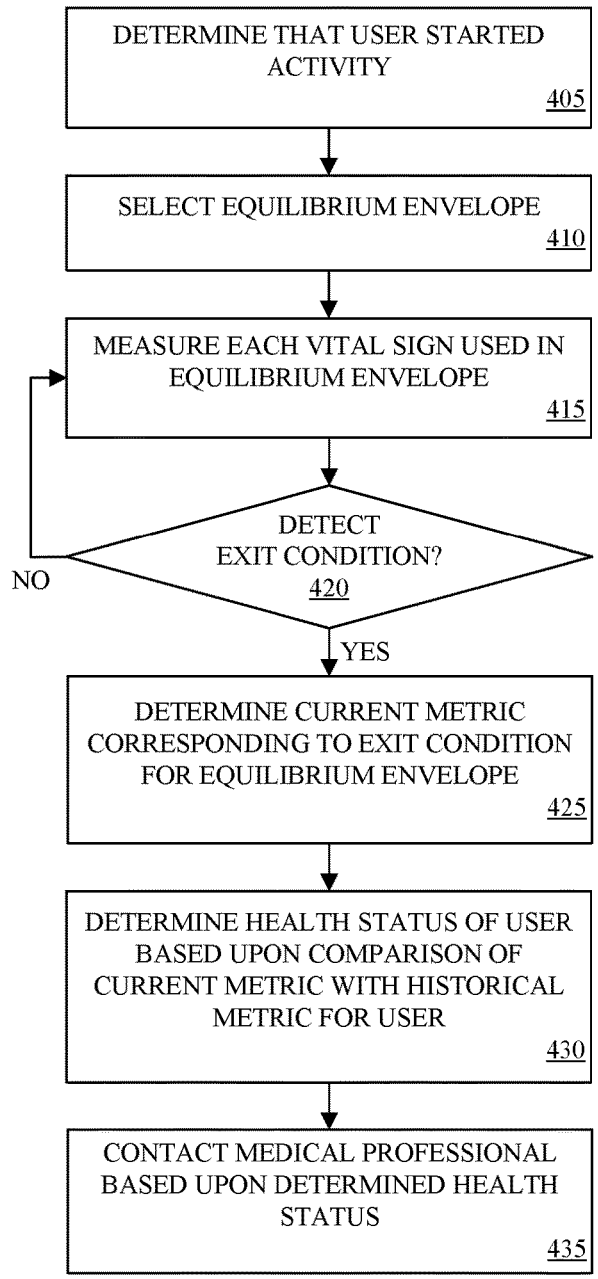
FIG. 4 illustrates an example method for evaluating health of a user.

FIG. 4 illustrates an example method 400 for evaluating health of a user. Method 400 can be performed by device 100 as described in connection with FIG. 1. Method 400 is directed to embodiments where the device determines one or more metrics relating to an exit condition for the equilibrium envelope. As such, method 400 begins in a state where one or more equilibrium envelopes for the user of the device has been generated. Further, the user is either carrying or wearing the device so that the device is capable of measuring two or more of the vital signs described herein.

In block 405, the device determines that the user has started performing an activity. In one or more embodiments, the device is capable of automatically determining that the user has started performing an activity. For example, the device may monitor accelerometer data and/or GPS data to determine whether the user has started an activity based upon the amount of movement detected, amount of energy expended (e.g., from the accelerometer), or based upon other sensor data.

In particular embodiments, the device is capable of automatically determining the particular activity being performed by the user. For example, the device is capable of determining whether the user is performing a particular activity such as walking, running, or dressing. In one or more embodiments, the device is capable of storing multiple different equilibrium envelopes for the user where each equilibrium envelope is specific to a particular activity. The device is capable of matching sensor data from one or more motion sensors, for example, with previously stored sensor data collected while the user performs different activities to form an activity profile. Thus, the device is capable of detecting that the user has started an activity and is capable of matching the activity to a particular equilibrium envelope available to or within the device for the activity. This allows the device to utilize one equilibrium envelope for walking, another equilibrium envelope for running, another equilibrium envelope for bathing, and so on.

In one or more embodiments, the device is capable of receiving one or more user inputs providing data indicating that the user has started an activity. The data further may indicate a particular type of activity that the user has started. For example, the data can indicate the time that an activity has started and the type of activity, e.g., walking, running, another form of exercise, or a daily activity such as bathing.

In block 410, the device optionally selects an equilibrium envelope. For example, in the case where the user has more than one different equilibrium envelope and each different equilibrium envelope is associated with a different activity, the device selects the particular equilibrium envelope that matches the activity determined in block 405. As discussed, in one or more embodiments, the user is associated with a single equilibrium envelope and, in such cases, the device uses, or selects, this equilibrium envelope.

In one or more embodiments, an equilibrium envelope for a user may include or specify a past or historical PE level for the user. In the case where a single equilibrium envelope is available, the PE level may be a PE level for the user that is obtained from the user during a prior instance or prior instances where the user performed sufficient activity to exit an equilibrium envelope. In cases where there are multiple equilibrium envelopes and each is activity specific, the PE level may be a PE level for the user that is obtained from the user during a prior instance or prior instances where the user performed the specific activity corresponding to the equilibrium envelope and exited the equilibrium envelope. For example, in either case, the PE level may be obtained at or about the time that the user exits the equilibrium envelope. In particular embodiments, the equilibrium envelope may be associated with a PE level for the user as opposed to including the PE level.

In block 415, the device measures each vital sign used in the equilibrium envelope. As an illustrative and non-limiting example, the equilibrium envelope may specify a range for each of heart rate (HR), systolic blood pressure (BP), and respirator rate. The equilibrium envelope may be specified as {[HR: 63-72]; [BP: 102-112]; [respiratory rate: 14-17]}.

In block 420, the device detects whether an exit condition for the equilibrium envelope has occurred. More particularly, in block 420, the device determines whether one or more of the vital signs measured in block 415 is outside of the range for that vital sign per the equilibrium envelope. The device determines that an exit condition has occurred in response to determining that at least one of the vital signs is outside of the range for that vital sign per the equilibrium envelope. In response to determining that one or more of the vital signs, as measured in block 415, is outside of the corresponding range for the vital sign specified by the equilibrium envelope, method 400 continues to block 425. In response to determining that none of the vital signs, as measured in block 415, is outside of the corresponding range for the vital sign specified by the equilibrium envelope, method 400 loops back to block 415 to continue measuring the vital signs.

For example, if the vital signs measured in block 415 are {[HR=65]; [BP=70]; [respirator rate=15]}, then an exit condition has not occurred. If the vital signs measured in block 505 are {[HR=65]; [BP=70]; [respirator rate=18]}, then an exit condition has occurred. As discussed, an exit condition occurs when one or more vital signs is out of the range specified by the equilibrium envelope.

In block 425, the device determines a current metric corresponding to an exit condition for the equilibrium envelope. In one or more embodiments, the current metric is an amount of time. The current metric, for example, can specify an amount of time for the user to perform an activity for the exit condition to occur. The device is capable of measuring the amount of time that passes from the start of the user performing the activity in block 405 until the occurrence of the exit condition in block 420 as using the measured amount of time as the current metric.

In one or more embodiments, the current metric is a quantity of activity performed by the user. The current metric can specify a quantity of activity performed by the user for the exit condition to occur. The device is capable of measuring the quantity of activity performed by the user from the start of the user performing the activity in block 405 until the occurrence of the exit condition in block 420 and storing the measured quantity of activity as the current metric. The quantity of activity can be measured in any number of ways. For example, the device is capable of measuring quantity of an activity in terms of number of steps taken from the time that the activity starts to the occurrence of the exit condition. The device is capable of measuring the quantity of activity as power output, e.g., wattage, from the accelerometer from the start of user activity as determined in block 405 to the occurrence of the exit condition. The device is capable of measuring the quantity of activity performed by the user as distance traveled from the start of the activity to the occurrence of the exit condition.

In one or more embodiments, the current metric includes a current user PE level. For example, in response to detecting an exit condition, the device is capable of prompting the user for a user PE level. The device is capable of asking the user to enter a PE level in response to detecting the exit condition. As such, the current user PE level specifies the PE of the user at or about the time of the exit condition.

In block 430, the device determines the health status for the user based upon a comparison of the current metric with a historical metric for the user. The device is capable of determining whether the health status for the user has improved, declined, or remained generally unchanged based upon whether the current metric determined in block 425 has improved, declined, or remained largely unchanged compared to the historical metric.

In one or more embodiments, where the metric is time, the device is capable of comparing the time for the exit condition to occur (the current metric) with a prior measurement of the time for the exit condition to occur for the user (the historical metric). In the case of time, the device is capable of determining that the health status for the user has improved in response to determining that the current metric is longer than the historical metric or is longer than the historical metric by more than a predetermined amount. The device is capable of determining that the health status for the user has declined or worsened in response to determining that the current metric is shorter than the historical metric or that the historical metric is longer than the current metric by at least a predetermined amount. The device is capable of determining that the health status for the user has not changed or has not changed in a significant manner in response to determining that the current metric is the same as the historical metric (e.g., the current metric is within a predetermined amount or percentage of the historical metric).

In one or more embodiments, where the metric is quantity of activity, the device is capable of comparing the quantity of activity performed when the exit condition occurs (the current metric) with a prior quantity of activity performed by the user for the exit condition to occur (the historical metric). In the case of quantity of activity, the device is capable of determining that the health status for the user has improved in response to determining that the current metric is larger than the historical metric or is larger than the historical metric by more than a predetermined amount. The device is capable of determining that the health status for the user has declined or worsened in response to determining that the current metric is less than the historical metric or that the historical metric is more than the current metric by at least a predetermined amount. The device is capable of determining that the health status for the user has not changed or has not changed in a significant manner in response to determining that the current metric is the same as the historical metric (e.g., the current metric is within a predetermined amount or percentage of the historical metric).

In one or more embodiments, the current metric and the historical metric may be for a same activity for the user (e.g., and for a same equilibrium envelope). For example, the device may store the historical metric in association with the particular activity that was performed by the user when the metric was calculated. As such, the device is capable of performing the comparison of the current metric with the historical metric for the same activity. This prevents the system from comparing a current metric for jogging, for example, with the historical metric for walking.

In one or more embodiments, where the metric is user PE level, the device is capable of comparing the current user PE level (the current metric) with a prior measurement of the user PE level (the historical metric—e.g., the user PE level specified by and/or associated with the equilibrium envelope). In the case of user PE level, the device is capable of determining that the health status for the user has improved in response to determining that the current metric is lower than the historical metric or is lower than the historical metric by more than a predetermined amount. The device is capable of determining that the health status for the user has declined or worsened in response to determining that the current metric is higher than the historical metric or that the historical metric is higher than the current metric by at least a predetermined amount. The device is capable of determining that the health status for the user has not changed or has not changed in a significant manner in response to determining that the current metric is the same as the historical metric (e.g., the current metric is within a predetermined amount or percentage of the historical metric).

In block 435, the device optionally contacts a designated contact based upon the health status determined in block 430. For example, the device is capable of sending a message such as an electronic mail, a text message, an instant message, to the system or device of a designated (e.g., a user selected or otherwise enumerated) third party, whether a designated medical professional, a friend, or a relative. In another example, the device is capable of initiating a phone call, either itself or via another device communicatively linked thereto, to send a message to a phone or a system of a designated contact. The device may also provide notifications to the user indicating health status and/or that a designated contact was contacted.

In one or more embodiments, the content of the message can include the health status determined in block 430. In one or more embodiments, the device is capable of sending the message in response to detecting a change in health status. For example, the device may send the message in response to detecting an improvement in health status for the user. In another example, the device may send the message in response to detecting a decline in health status for the user. In another example, the device may send the message in response to detecting either an improvement or a decline in the health status for the user. In another example, the device may send a message describing the detected health status. For example, the device may specify any detected change in user PE level and/or any detected change in exit condition whether based upon time or amount of energy within the message.

In particular embodiments, the degree of change, as determined by the amount of change in the current metric compared to the historical metric, can be used to trigger the sending of the message by the user's device. For example, the device may send a message only in response to detecting a change in health status of more than a threshold amount. The device may use one threshold amount when evaluating change in improvement in health status and another different threshold amount when evaluating change in a decline in health status. Thus, a small change when health status declines may trigger the sending of a message, while a larger change is required when health status improves to trigger a message. In one or more other embodiments, the device is capable of using different threshold amounts based upon the particular activity that is performed. For example, smaller changes may trigger the sending of a message when evaluating health status for everyday activities such as bathing, while larger changes may trigger the sending of a message when evaluating health status for more rigorous exercise.

Figure 5:
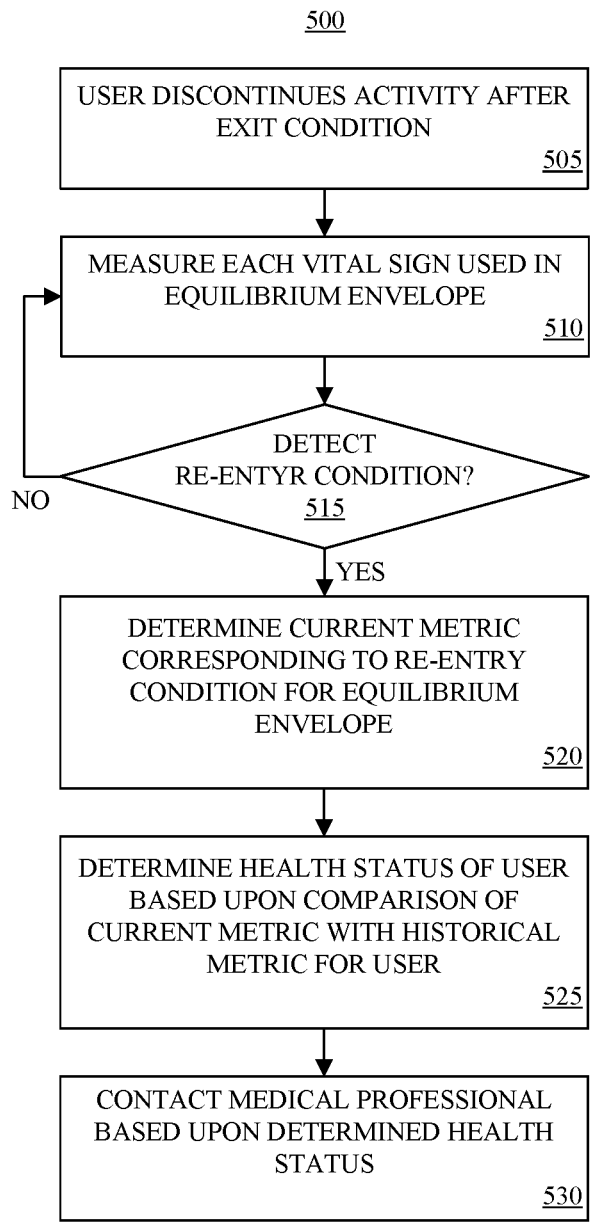
FIG. 5 illustrates another example method for evaluating health of a user.

FIG. 5 illustrates another example method 500 for evaluating health of a user. Method 500 can be performed by device 100 as described herein in connection with FIG. 1. Method 500 is directed to embodiments where the device determines one or more metrics relating to a re-entry condition. Further, the user is either carrying or wearing the device so that the device is capable of measuring two or more of the vital signs described herein.

In block 505, the device determines that the user has discontinued activity after the occurrence of an exit condition. In one or more embodiments, the device is capable of automatically determining that the user has discontinued performing the activity, e.g., the activity that caused the exit condition to occur. For example, the device may monitor accelerometer data and/or GPS data to determine whether the user has discontinued the activity based upon amount of movement, power output from the accelerometer, or other sensor data. In one or more embodiments, the device is capable of receiving data specified by a user input indicating that the user has discontinued the activity.

In block 510, the device measures each vital sign used in the equilibrium envelope. For example, the device can determine vital signs including, but not limited to, any combination of two or more of heart rate, blood pressure, respiration, heart rate variability, oxygen saturation, and blood glucose. As discussed, the device is capable of determining current measurements of any two or more of the listed vital signs as specified by the equilibrium envelope.

In block 515, the device detects whether a re-entry condition for the equilibrium envelope has occurred. More particular, in block 515, the device is capable of determining whether each of the vital signs is within the range for that vital sign as specified by the equilibrium envelope. The device determines that a re-entry condition has occurred in response to determining that the current measure of each vital sign of the equilibrium envelope is within the range for that vital sign as specified by the equilibrium envelope. If the device determines that each of the vital signs is within the range for the relevant vital sign per the equilibrium envelope, method 500 continues to block 520. If the device determines that one or more of the vital signs is outside of the range for the relevant vital sign per the equilibrium envelope, method 500 loops back to block 510 to continue measuring vital signs used in the equilibrium envelope.

By checking whether each vital sign of the equilibrium envelope is within range, the device is capable of detecting conditions where the user is not fully recovered from performing activity. For example, heart rate of the user may have recovered to a value within the range for heart rate in the equilibrium envelope, while the blood pressure or the respiration for the user is still outside of the appropriate range per the equilibrium envelope. The user, for example, may still be "out of breath" and have a respiratory rate that exceeds the range of the equilibrium envelope. In that case, the re-entry condition has not yet occurred for the user.

For purposes of illustration, Table 1 illustrates example vital signs measured for a user as performed for block 510 over time of T1 to T5. As an illustrative example, the vital signs may be measured each minute or at some other time interval less than one minute or greater than one minute. The equilibrium envelope may be the same as described above, i.e., {[HR: 63-72]; [BP: 102-112]; [respiratory rate: 14-17]}.

TABLE 1

| Time | Heart Rate | Systolic Blood Pressure | Respiration |
|---|---|---|---|
| 1 | 90 | 130 | 25 |
| 2 | 85 | 120 | 22 |
| 3 | 78 | 110 | 20 |
| 4 | 70 | 110 | 18 |
| 5 | 70 | 110 | 16 |

As illustrated, at times T1 and T2, each of the vital signs for the user is outside of the corresponding range per the equilibrium envelope. At time T3, heart rate and respiration are outside of the corresponding ranges, while blood pressure is within the range for blood pressure per the equilibrium envelope. At time T4, respiration remains out of range, while both heart rate and blood pressure are within the appropriate ranges per the equilibrium envelope. At time T5, since each of heart rate, blood pressure, and respiration is within the corresponding range per the equilibrium envelope, the device determines that a re-entry condition has occurred.

In block 520, the device determines a metric corresponding to the re-entry condition for the equilibrium envelope. In one or more embodiments, the device calculates the amount of time that elapsed from the time the user discontinued activity as determined in block 505 to the time when the re-entry condition occurs in block 515 (e.g., the "yes" branch). The amount of time measured is used as the current metric.

In block 525, the device determines the health status for the user based upon a comparison of the current metric with a historical metric for the user. The device is capable of determining whether the health status for the user has improved, declined, or remained generally unchanged based upon whether the current metric determined in block 720 has improved, declined, or remained largely unchanged compared to the historical metric.

If, for example, the current metric is longer than the historical metric, the device determines that the health status for the user has worsened since the user requires more time than in the past to recover from the activity. If, for example, the current metric is shorter than the historical metric, the device determines that the health status for the user has improved since the use requires less time to recover from the activity. If, for example, the current metric is the same as the historical metric (e.g., within a predetermined amount or percentage of the prior metric) the device determines that the health status for the user has remained the same or substantially the same.

In block 530, the device optionally contacts a designated contact based upon the health status determined in block 525. For example, the device is capable of sending a message such as an electronic mail, a text message, an instant message, to the system or device of a designated (e.g., a user selected or otherwise enumerated) third party, whether a designated medical professional, a friend, or a relative. In another example, the device is capable of initiating a phone call, either itself or via another device communicatively linked thereto, to send a message to a phone or a system of a designated contact.

In one or more embodiments, the content of the message can include the health status determined in block 525. In one or more embodiments, the device is capable of sending the message in response to detecting a change in health status. For example, the device may send the message in response to detecting an improvement in health status for the user. In another example, the device may send the message in response to detecting a decline in health status for the user. In another example, the device may send the message in response to detecting either an improvement or a decline in the health status for the user. The device may also provide notifications to the user indicating health status and/or that a designated contact was contacted.

In particular embodiments, the degree of change, as determined by the amount of change in the current metric compared to the historical metric, can be used to trigger the sending of the message by the user's device. For example, the device may send a message only in response to detecting a change in health status of more than a threshold amount. The device may use one threshold amount when evaluating change in improvement in health status and another different threshold amount when evaluating change in a decline in health status. Thus, a small change when health status declines may trigger the sending of a message, while a larger change is required when health status improves to trigger a message. In one or more other embodiments, the device is capable of using different threshold amounts based upon the particular activity that is performed. For example, smaller changes may trigger the sending of a message when evaluating health status for everyday activities such as bathing, while larger changes may trigger the sending of a message when evaluating health status for more rigorous exercise.

The inventive arrangements described within this disclosure facilitate a contextual analysis of physiological health of the user. The contextual analysis evaluates relative changes vital signs compared to baselines of such vital signs specified by the equilibrium envelope for the user. As such, the device is capable of detecting changes in health status for the user based upon comparisons of the metrics described in response to exertion, life style etiology, and/or pathological exacerbation. In this manner, the device is capable of not only detecting changes in health status that may occur due to lifestyle choices, but also changes in health status that are attributable to disease flare up.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise.

As defined herein, the term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The various forms of memory, as described herein, are examples of computer readable storage media. A non-exhaustive list of more specific examples of a computer readable storage medium may include: a portable computer diskette, a hard disk, a RAM, a read-only memory (ROM), an erasable programmable read-only memory (EPROM or Flash memory), an electronically erasable programmable read-only memory (EEPROM), a static random-access memory (SRAM), a portable compact disc read-only memory (CD-ROM), a digital versatile disk (DVD), a memory stick, a floppy disk, or the like.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the term "responsive to" and similar language as described above, e.g., "if," "when," or "upon," means responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

As defined herein, the terms "one embodiment," "an embodiment," "one or more embodiments," "particular embodiments," or similar language mean that a particular feature, structure, or characteristic described in connection with the embodiment is included in at least one embodiment described within this disclosure. Thus, appearances of the phrases "in one embodiment," "in an embodiment," "in one or more embodiments," "in particular embodiments," and similar language throughout this disclosure may, but do not necessarily, all refer to the same embodiment. The terms "embodiment" and "arrangement" are used interchangeably within this disclosure.

As defined herein, the term "output" means storing in physical memory elements, e.g., devices, writing to display or other peripheral output device, sending or transmitting to another system, exporting, or the like.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field programmable gate array (FPGA), a programmable logic array (PLA), an application specific integrated circuit (ASIC), programmable logic circuitry, and a controller.

As defined herein, the term "real-time" means a level of processing responsiveness that a user or system senses as sufficiently immediate for a particular process or determination to be made, or that enables the processor to keep up with some external process.

As defined herein, the term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

As defined herein, the term "user" means a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a Local Area Network (LAN), a Wide Area Network (WAN) and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowchart or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method for evaluating health of a user, comprising:
    tracking a plurality of vital signs of a user using a plurality of sensors of a device, wherein the plurality of vital signs are determined from sensor data generated by the plurality of sensors;
    storing an equilibrium envelope for the user in a memory of the device with the plurality of vital signs, wherein the equilibrium envelope includes a range for each of a plurality of vital signs for the user and historical metric data, wherein each range indicates homeostatic equilibrium for the user while at rest for one of the plurality of vital signs;
    detecting, using a processor of the device in real-time, the user starting an activity based on the sensor data;
    in response to detecting the activity, detecting, using the processor and based on the sensor data, an exit condition for a selected vital sign of the plurality of vital signs, wherein the exit condition is the selected vital sign exiting the range of the equilibrium envelope corresponding to the selected vital sign;
    determining an amount of time for the exit condition to occur measured from a start of the activity; and
    determining, using the processor, a health status for the user based upon the amount of time for the exit condition to occur for the selected vital sign compared to a historical amount of time for the exit condition to occur for the selected vital sign from the historical metric data of the equilibrium envelope.

2. The method of claim 1, wherein the sensor data includes a photoplethysmogram.

3. The method of claim 1, wherein the selected vital sign is heart rate.

4. The method of claim 1, comprising:
    determining an amount of work performed by the user from a time that the activity was detected to the exit condition; and
    wherein the health status of the user is further based on the amount of work performed.

5. The method of claim 1, comprising:
    detecting a re-entry condition based on the sensor data, wherein the re-entry condition is, subsequent to the exit condition, the user discontinuing the activity while one or more of the plurality of vital signs is outside of the range for the vital sign per the equilibrium envelope and each vital sign of the plurality of vital signs entering the range for the vital sign.

6. The method of claim 5, comprising:
    determining an amount of time for the re-entry condition to occur after the user discontinues the activity; and
    wherein the health status of the user is further based on the amount of time for the re-entry condition to occur.

7. The method of claim 1, wherein the plurality of vital signs includes heart rate and blood pressure.

8. The method of claim 7, wherein the plurality of vital signs further includes respiration rate.

9. The method of claim 8, wherein the plurality of vital signs further includes heart rate variability, oxygen saturation, and blood glucose.

10. A device, comprising:
    a memory configured to store instructions;
    a plurality of sensors configured to collect sensor data for a user; and
    a processor coupled to the memory, wherein the processor, in response to executing the instructions, is configured to initiate operations for evaluating health of the user including:
    tracking a plurality of vital signs of the user using the plurality of sensors, wherein the plurality of vital signs are determined from sensor data generated by the plurality of sensors;
    storing an equilibrium envelope for the user in the memory with the plurality of vital signs, wherein the equilibrium envelope includes a range for each of a plurality of vital signs for the user and historical metric data, wherein each range indicates homeostatic equilibrium for the user while at rest for one of the plurality of vital signs;
    detecting, in real-time, the user starting an activity based on the sensor data;
    in response to detecting the activity, detecting, based on the sensor data, an exit condition for a selected vital sign of the plurality of vital signs, wherein the exit condition is the selected vital sign exiting the range of the equilibrium envelope corresponding to the selected vital sign;

determining an amount of time for the exit condition to occur measured from a start of the activity; and determining a health status for the user based upon the amount of time for the exit condition to occur for the selected vital sign compared to a historical amount of time for the exit condition to occur for the selected vital sign from the historical metric data of the equilibrium envelope.

11. The device of claim 10, wherein the sensor data includes a photoplethysmogram.

12. The device of claim 10, wherein the selected vital sign is heart rate.

13. The device of claim 10, wherein the processor is configured to initiate operations comprising:

determining an amount of work performed by the user from a time that the activity was detected to the exit condition; and wherein the health status of the user is further based on the amount of work performed.

14. The device of claim 10, wherein the processor is configured to initiate operations comprising:

detecting a re-entry condition based on the sensor data, wherein the re-entry condition is, subsequent to the exit condition, the user discontinuing the activity while one or more of the plurality of vital signs is outside of the range for the vital sign per the equilibrium envelope and each vital sign of the plurality of vital signs entering the range for the vital sign.

15. The device of claim 14, wherein the processor is configured to initiate operations comprising:

determining an amount of time for the re-entry condition to occur after the user discontinues the activity; and wherein the health status of the user is further based on the amount of time for the re-entry condition to occur.

16. The device of claim 10, wherein the plurality of vital signs includes heart rate and blood pressure.

17. The device of claim 16, wherein the plurality of vital signs further includes respiration rate.

18. The device of claim 17, wherein the plurality of vital signs further includes heart rate variability, oxygen saturation, and blood glucose.

19. A computer program product comprising a computer readable storage medium having program code stored thereon for evaluating health of a user, the program code executable by a processor to perform operations comprising:

tracking a plurality of vital signs of the user using a plurality of sensors of a device, wherein the plurality of vital signs are determined from sensor data generated by the plurality of sensors;

storing an equilibrium envelope for the user in a memory of the device with the plurality of vital signs, wherein the equilibrium envelope includes a range for each of a plurality of vital signs for the user and historical metric data, wherein each range indicates homeostatic equilibrium for the user while at rest for one of the plurality of vital signs;

detecting, using a processor of the device in real-time, the user starting an activity based on the sensor data;

in response to detecting the activity, detecting, based on the sensor data, an exit condition for a selected vital sign of the plurality of vital signs, wherein the exit condition is the selected vital sign exiting the range of the equilibrium envelope corresponding to the selected vital sign;

determining an amount of time for the exit condition to occur measured from a start of the activity; and determining a health status for the user based upon the amount of time for the exit condition to occur for the selected vital sign compared to a historical amount of time for the exit condition to occur for the selected vital sign from the historical metric data of the equilibrium envelope.

20. The computer program product of claim 19, wherein the sensor data includes a photoplethysmogram.

21. The computer program product of claim 19, wherein the selected vital sign is heart rate.

22. The computer program product of claim 19, wherein the program code is executable by a processor to perform operations comprising:

determining an amount of work performed by the user from a time that the activity was detected to the exit condition; and wherein the health status of the user is further based on the amount of work performed.

23. The computer program product of claim 19, wherein the program code is executable by a processor to perform operations comprising:

detecting a re-entry condition based on the sensor data, wherein the re-entry condition is, subsequent to the exit condition, the user discontinuing the activity while one or more of the plurality of vital signs is outside of the range for the vital sign per the equilibrium envelope and each vital sign of the plurality of vital signs entering the range for the vital sign.

24. The computer program product of claim 23, wherein the program code is executable by a processor to perform operations comprising:

determining an amount of time for the re-entry condition to occur after the user discontinues the activity; and wherein the health status of the user is further based on the amount of time for the re-entry condition to occur.

25. The computer program product of claim 19, wherein the plurality of vital signs includes heart rate and blood pressure.

26. The computer program product of claim 25, wherein the plurality of vital signs further includes respiration rate.

27. The computer program product of claim 26, wherein the plurality of vital signs further includes heart rate variability, oxygen saturation, and blood glucose.

* * * * *